United States Patent
Pappne Behr et al.

(10) Patent No.: US 8,044,078 B2
(45) Date of Patent: Oct. 25, 2011

(54) AMINO-ALKYL AMIDE DERIVATIVES AS CCR3 RECEPTOR LIGANDS

(75) Inventors: Agnes Pappne Behr, Budapest (HU); Zoltan Kapui, Budapest (HU); Peter Aranyi, Budapest (HU); Sandor Batori, Budapest (HU); Veronika Bartane Bodor, Budapest (HU); Lajos T. Nagy, Budapest (HU); Mihalyne Santa, legal representative, Mezotur (HU); Marton Varga, Dunakeszi (HU); Endre Mikus, Budapest (HU); Katalin Urban-Szabo, Budapest (HU); Judit Vargane Szeredi, Budapest (HU); Tibor Szabo, Budapest (HU); Edit Susan, Dunakeszi (HU); Marianna Kovacs, Pomaz (HU)

(73) Assignee: Sanofi-Aventis, Paris (FR)

( * ) Notice: Subject to any disclaimer, the term of this patent is extended or adjusted under 35 U.S.C. 154(b) by 57 days.

(21) Appl. No.: 12/050,964

(22) Filed: Mar. 19, 2008

(65) Prior Publication Data

US 2008/0280961 A1    Nov. 13, 2008

Related U.S. Application Data

(63) Continuation of application No. PCT/HU2006/000079, filed on Sep. 19, 2006.

(30) Foreign Application Priority Data

Sep. 22, 2005 (HU) ..................................... 0500879

(51) Int. Cl.
*A61K 31/428* (2006.01)
*A61K 31/165* (2006.01)
*A61K 31/4184* (2006.01)
*A61P 31/18* (2006.01)
*C07D 277/68* (2006.01)
*C07D 235/26* (2006.01)
*C07C 233/00* (2006.01)

(52) U.S. Cl. ........ 514/367; 514/395; 514/619; 548/171; 548/306.4; 564/167

(58) Field of Classification Search .................. 514/367, 514/619, 395; 548/171, 306.4; 564/167
See application file for complete search history.

(56) References Cited

U.S. PATENT DOCUMENTS

| | | | |
|---|---|---|---|
| 5,389,630 A | 2/1995 | Sato et al. | |
| 6,166,015 A | 12/2000 | Rogers et al. | |
| 6,225,334 B1 | 5/2001 | Seitz et al. | |
| 2003/0119885 A1 | 6/2003 | Du Bois | |
| 2003/0171413 A1* | 9/2003 | Owen et al. | 514/367 |
| 2008/0280963 A1* | 11/2008 | Pappne Behr et al. | 514/375 |
| 2008/0287434 A1* | 11/2008 | Pappne Behr et al. | 514/233.2 |

FOREIGN PATENT DOCUMENTS

| | | |
|---|---|---|
| DE | 19629464 | 1/1998 |
| HU | 220592 | 7/1990 |
| WO | WO 9202487 | 2/1992 |
| WO | WO 9822433 | 5/1998 |
| WO | WO 0053600 | 9/2000 |
| WO | WO 0109088 | 2/2001 |
| WO | WO 0114333 | 3/2001 |
| WO | WO 0187839 | 11/2001 |
| WO | WO 02/59081 | 8/2002 |
| WO | WO 2004004731 | 1/2004 |
| WO | WO 2007034252 A1 * | 3/2007 |

OTHER PUBLICATIONS

Vippagunta et al., Advanced Drug Delivery Reviews, vol. 48, p. 3-26 ( on p. 3).*
Vippagunta et al., Advanced Drug Delivery Reviews, (2001), vol. 48, p. 3-26 ( on p. 3), provided previously.*
RN 142196-21-2 (Jul. 3, 1992).
RN 737754-09-5 (2006).
RN 686727-21-9 (Apr. 25, 2003).
RN 371244-71-2 (Nov. 21, 2001).

* cited by examiner

*Primary Examiner* — Yong Chu
(74) *Attorney, Agent, or Firm* — Scully, Scott, Murphy & Presser, P.C.

(57) ABSTRACT

The invention relates to a compound of the general formula (I),

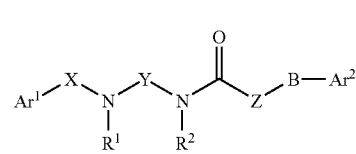

as defined herein which is useful for the treatment of a pathology in a patient wherein a CCR3 receptor plays a role in the development of the pathology, and pharmaceutical preparations containing such compound. The invention is also directed to a process for preparing the compound of the general formula (I), and intermediate useful in the preparation.

4 Claims, No Drawings

AMINO-ALKYL AMIDE DERIVATIVES AS CCR3 RECEPTOR LIGANDS

FIELD OF THE INVENTION

The present invention relates to the CCR3 receptor ligands of general formula (I), within them favourably antagonists and to the salts, solvates and isomers thereof, to the pharmaceutical compositions containing them, to the use of the compounds of the general formula (I) and their salts, solvates and isomers and to the preparation of the compounds of the general formula (I) and their salts, solvates and isomers.

BACKGROUND OF THE INVENTION

Chemokines are small molecular weight (8-12 kDa) secreted polypeptides playing important regulatory role in the immune processes due to their leukocyte attracting (chemotactic) effect. They exert their effects through the chemokine receptors, which belong to the family of the G protein coupled receptors.

The CC chemokine receptors 3 (CCR3 receptors) are expressed by a number of inflammatory cells, like the basofils, mast cells, T lymphocytes, epithelial cells, dendritic cells, but in the greatest amount they can be found on the surface of the eosinofiles.

The CCR3 receptor ligands belong to the family of the C—C kemokines. They have a number of selective and non-selective ligands. The selective ligands are the eotaxin, eotaxin-2 and the lately discovered eotaxin-3. The non-selective ligands are the RANTES, the monocyte chemotactic proteins (MCP-2, MCP-3, MCP-4) and the macrophag inhibitor protein (MIP-1). The best characterized CCR3 ligand known from a long time is the eotaxin.

The eotaxin through the activation of the CCR3 receptors attracts selectively the eosinofils. Prior to an allergen provocation, the measured eotaxin level in the broncho-alveolar lavage fluidum of asthmatic patients was by 67 percent higher. On the effect of provocation a 2.4-fold increase of the epithelial and endothelial cells of the respiratory tract were found.

In the lung the eotaxin is produced in many cells. Following an allergen response, the most important eotaxin sources are the epithelial cells, but a great amount of eotaxin is produced by the fibroblasts of the lung, the smooth muscle cells and the endothelial cells of the respiratory tract, the alveolar macrophags and lymphocytes, and the eosinofils themselves.

Originally the data showed that the CCR3 receptors are to be found only in the eosinofil cells (Bertrand C P, Ponath P D., Expert Opin Investig Drugs. 2000 January; 9(1):43-52.), but on the basis of expression profiles it has been revealed that other inflammatory cells—although in smaller amount—also contain CCR3 receptors (Elsner J, Escher S E, Forssmann U., Allergy. 2004 December; 59(12):1243-58.). Thus, the CCR3 antagonists possess much wider effect, their activity is not limited to the eosinofils and consequently they can be considered much more valuable and effective targets in the treatment of asthmatic, allergic and inflammatory diseases.

Based on the above observations, CCR3 antagonists may possess important profilactic and therapeutic effects in the treatment of pathologies where in the development of the disease CCR3 receptors play a role. These diseases are characterized by the disorder of the leucocyte functions (activation, chemotaxis), there are numerous chronic inflammatory diseases among them, such as asthma, allergic rhinitis, atopic dermatitis, eczema, inflammatory bowel disease, ulcerative colitis, allergic conjunctivitis, arthritis, multiple sclerosis, Crohn's disease, HIV-infection and diseases in conjunction with AIDS.

The CCR3 antagonists published to date in the literature are carbamide-, thiocarbamide derivatives (WO 01/09088, WO 02/059081) and/or compounds containing saturated cyclic amino group (WO 00/35451, U.S. Pat. No. 6,605,623, WO 01/98270, WO 03/004487, WO 03/018556, WO 2004/028530, WO 00/53600, WO 00/35876, WO 01/64216, WO 02/50064, WO 02/102775, GB 2373186, WO 03/082291, WO 2004/004731, WO 2004/058702, WO 2004/085423). The present invention relates to a new structural type of compounds, to the open-chain amino-alkyl-amide derivatives, representatives of these compounds are effective CCR3 receptor antagonists.

From the aspect of therapeutic use it is essential that the molecules do not bind, or bind only in case of very high concentration to other the CCR receptor subtypes.

Our aim was to prepare compounds of high antagonistic activity, and at the same time selective to the CCR3 receptor, i.e. which inhibit the CCR3 receptor in much smaller concentration as compared to other CCR receptors. Further aim was that the new compounds have stability, bioavailability, therapeutic index and toxicity values which ensure its drugability. Additional aim was that the compounds, through their good enteric absorption can be applied orally.

SUMMARY OF THE INVENTION

We have found that the compounds of general formula (I),

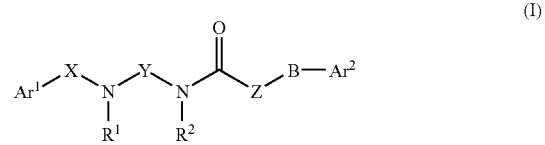

wherein

B stands for oxygen atom or —NR$^6$— group, wherein R$^6$ means hydrogen atom or straight or branched C$_{1-4}$ alkyl group;

Ar$^1$ stands for phenyl group optionally substituted with one or more halogen atom;

X and Y independently mean straight C$_{1-4}$ alkylene group optionally substituted with one or more identical or non-identical straight or branched C$_{1-4}$ alkyl group;

Z stands for a straight C$_{1-4}$ alkylene group optionally substituted with one or more identical or non-identical straight or branched C$_{1-4}$ alkyl group;

R$^1$ and R$^2$ independently mean hydrogen atom or straight or branched C$_{1-4}$ alkyl group;

Ar$^2$ stands for phenyl- or benzyl group, optionally substituted with halogen atom; 5- or 6-membered heterocyclic ring containing one, two, or three nitrogen atoms, or two nitrogen atoms and one oxygen atom, or one nitrogen atom and one oxygen atom, or one nitrogen atom and one sulphur atom, optionally substituted with one or more identical or non-identical substituents selected from the group consisting of straight or branched C$_{1-4}$ alkyl group, amino group, amino group-substituted with one or two identical or non-identical straight or branched C$_{1-4}$ alkyl group-, and benzyl group-optionally substituted with straight or branched C$_{1-4}$ alkoxy group or halogen atom-; benzologue of the 5- or 6-membered heterocyclic ring group wherein the benzene ring may optionally be further substituted with one or more identical or non-identical substituents selected from the group consisting of straight or branched $C_{1-4}$ alkyl group, straight or branched $C_{1-4}$ alkoxy group, hydroxyl group, amino group, amino group-substituted with one or two identical or non-identical straight or branched $C_{1-4}$ alkyl group-, and halogen atom;

5-membered heterocyclic ring containing one, two or three nitrogen atoms, or one nitrogen atom and one oxygen atom, or one nitrogen atom and one sulphur atom, condensed with a 6-membered heteroaromatic ring group containing one or two nitrogen atoms, optionally substituted with one or more identical or non-identical substituents selected from the group consisting of straight or branched $C_{1-4}$ alkyl group, straight or branched $C_{1-4}$ alkoxy group, hydroxyl group, amino group, and amino group-substituted with one or two identical or non-identical straight or branched $C_{1-4}$ alkyl group or benzyl group-;

and their salts, solvates and isomers and the salts and solvates thereof fulfil the above criteria.

DETAILED DESCRIPTION OF THE INVENTION

The detailed meanings of the above substituents are as follows:

By a $C_{1-4}$ alkyl group we mean a saturated straight- or branched-chain aliphatic group of 1-4 carbon atom, such as methyl-, ethyl-, propyl-, isopropyl-, butyl-, isobutyl-, secondary butyl-, tertiary butyl group.

By a $C_{1-4}$ alkylene group we mean a —$(CH_2)_n$— group where the value of n is 1, 2, 3 or 4, such as a methylene-, ethylene-, propylene-, butylene group.

By a $C_{1-4}$ alkoxy group we mean an —O-alkyl group— where the meaning of alkyl is as defined above-, such as methoxy-, ethoxy-, propoxy-, isopropoxy-, butoxy-, isobutoxy-, secondary butoxy-, tertiary butoxy group.

By halogen atom we mean chloro, fluoro, iodo or bromo atom.

By a 5- or 6-membered heterocyclic ring containing one, two or three nitrogen atoms we mean an unsaturated, saturated or partially saturated heterocyclic ring, for example pyrrole, imidazole, pyrazole, 1,2,3-triazole, 1,2,4-triazole, pyridine, pyrimidine, pyridazine, pyrazine 1,2,4-triazine, 1,3,5-triazine, 1,2,3-triazine, pyrrolidine, imidazolidine, 1,2,4-triazolidine, piperidine, piperazine, 2-imidazoline ring.

By a 5- or 6-membered heterocyclic ring containing one nitrogen atom and one oxygen or sulphur atom we mean an unsaturated, saturated or partially saturated heterocyclic ring, for example oxazole, isoxazole, thiazole, isothiazole, 1,2-oxazine, 1,3-oxazine, 1,4-oxazine, 1,2-thiazine, 1,3-thiazine, 1,4-thiazine, oxazolidine, thiazolidine, morpholine, thiomorpholine, 2-thiazoline, 2-oxazoline ring.

The heterocyclic ring containing two nitrogen atoms and one oxygen atom may be for example an oxadiazole ring.

By benzologue we mean derivatives condensed with benzene ring, for example indole, benzoxazole, benzthiazole, benzimidazole, quinoline, quinazoline, quinoxaline.

A derivative of a 5-membered heterocyclic ring-containing one, two or three nitrogen atoms, or one nitrogen atom and one oxygen atom, or one nitrogen atom and one sulphur atom—condensed with 6-membered heterocyclic rings-containing one or two nitrogen atom, may for example be thiazolopyridine, triazolopyridine, thiazolopyrimidine, oxazolopyridine, 9H-purine, 3H-imidazopyridine.

By salts of the compounds of general formula (I) we mean salts given with inorganic and organic acids and bases. Preferable are the salts formed with pharmaceutically acceptable acids e.g. hydrochloric acid, sulfuric acid, ethanesulfonic acid, tartaric acid, fumaric acid, citric acid, and bases e.g. sodium hydroxide, potassium hydroxide, ethanolamine. The salts formed during the purification and isolation process, favourably with tetrafluoroboric acid and perchloric acid, are also subjects of the invention.

By solvates we mean solvates formed with various solvents, e.g. with water or ethanol.

By isomers we mean structural and optical isomers. Structural isomers may be tautomeric forms in equilibrium or isolated desmotrops, which are also subjects of the invention. The compounds of general formula (I) may contain one or more asymmetric carbon atom, thus they may be optical isomers, enantiomers or diastereoisomers. These enantiomers and diastereoisomers and the mixtures thereof, including the racemates are also subjects of the invention.

Especially favourable are the following compounds:

N-{3-[(3,4-Dichlorobenzyl)(methyl)amino]propyl}-2-(1,3-benzoxazol-2-yl)-amino]acetamide;

$N^1$-{3-[(3,4-Dichlorobenzyl)(methyl)amino]propyl-$N^2$-(6-methyl-1,3-benzothiazol-2-yl)-glycinamide;

2-[(1,3-Benzoxazol-2-yl)oxy]-N-{3-[(3,4-dichlorobenzyl)(methyl)amino]propyl}-acetamide;

2-(1,3-Benzthiazol-2-yloxy)-N-{3-[(3,4-dichlorobenzyl)(methyl)amino]propyl}acetamide; and their salts, solvates and isomers and the salts and solvates thereof.

The present invention relates furthermore to the pharmaceutical preparations containing the compounds of the general formula (I) or its isomers, salts or solvates, which are preferably oral preparations, but inhalable, parenteral and transdermal preparation also form a subject of the present invention. The above pharmaceutical preparations may be solid or liquid formulations, for example tablets, pellets, capsules, patches, solutions, suspensions or emulsions. The solid formulations, first of all the tablets and capsules are preferred.

The above pharmaceutical preparations are prepared by applying the usual excipients and technological operations.

The compounds of the general formula (I) according to the invention can be used for the treatment of pathologies where CCR3 receptors play a role in the development of the disease.

The compounds according to the present invention can favourably used in the treatment of diseases like asthma, allergic rhinitis, atopic dermatitis, eczema, inflammatory bowel disease, ulcerative colitis, allergic conjunctivitis, multiple sclerosis, Crohn's disease, HIV-infection and diseases in conjunction with AIDS.

A further subject of the invention is the use of the compounds of the general formula (I) for the treatment of the above pathologies. The suggested daily dose is 1-100 mg of the active component, depending on the nature and severity of the disease and the sex and weight of the patient.

A further subject of the invention is the preparation of the compounds of general formula (I) and their salts, solvates and isomers.

The compounds according to the invention of general formulae (XX) and (XXI), used in process version c.) are novel, and they are also subjects of the invention. The meanings of the substituents of formulae (XX) and (XXI) are as defined above.

Scheme 1. presents one of the possible methods for the preparation of the compounds of general formula (I) (process version a.)

Scheme 1.

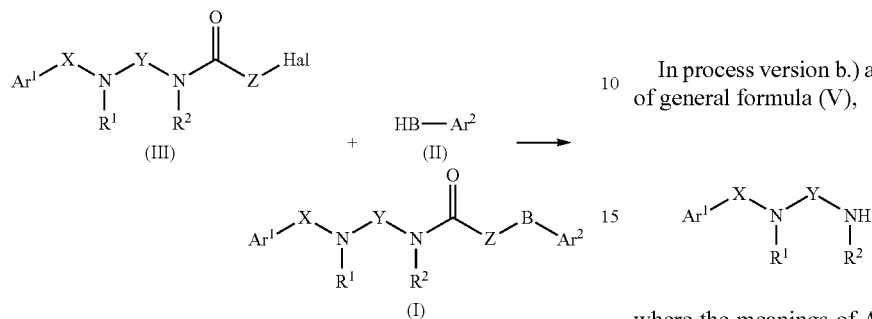

According to process version a.) a halogen compound of general formula (II),

(III)

where the meaning of Ar¹, X, Y, Z, R¹ and R² are as defined above and Hal represents a halogen atom, is reacted with a compound of general formula (II), HB—Ar²  (II)

where, the meanings of B and Ar² are as defined above, and if desired the substituents of the compound of general formula (I) thus obtained are transformed into each other by using known methods and/or the resulting compound of general formula (I) is transformed into its salt or solvate, or liberated from its salt or solvate and/or resolved into its optically active isomers, or the optically active isomer is transformed into the racemic compound and if desired the structural isomers are separated from each other.

Reaction a.) according to the invention is preferably carried out in an inert solvent such dichloromethane, chloroform, tetrahydrofuran, acetonitrile or in the mixture of thereof, preferably in N,N-dimethylformamide, in the presence of an organic base e.g. triethylamine or diethyl-i-propylamine, or of an inorganic base, preferably potassium carbonate, at a temperature between 0° C.-100° C., preferably at room temperature.

Scheme 2. presents another possible route for the preparation of the compounds of general formula (I) (process version b.).

Scheme 2.

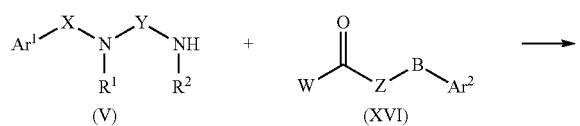

-continued

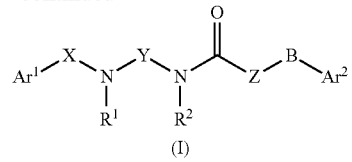

(I)

In process version b.) according to the invention a diamine of general formula (V),

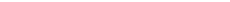

where the meanings of Ar¹, X, Y, R¹ and R² are as defined above is reacted with a carboxylic acid derivative of general formula (XVI),

where the meanings of Ar², Z and B are as defined above and W stands for halogen atom, hydroxyl group, —OR¹¹-group—where R¹¹ represents straight or branched $C_{1-4}$ alkyl group-, or —O—CO—Z-B—Ar²-group, where Z, B and Ar² have the meanings as defined above, and if desired the substituents of the compound of general formula (I) thus obtained are transformed into each other by using known methods and/or the resulting compound of general formula (I) is transformed into its salt or solvate, or liberated from its salt or solvate and/or resolved into its optically active isomers, or the optically active isomer is transformed into the racemic compound and if desired the structural isomers are separated from each other.

In a preferred embodiment of process version b.) according to the invention, the oxycarboxylic acids or aminocarboxylic acids of general formula (XVI), where W stands for hydroxyl group, are transformed with an acid chloride-forming reagent, preferably thionyl chloride, into the acid chloride, which is then reacted with the amine of general formula (V) in an inert solvent e.g. dichloromethane, chloroform, or ethylacetate, in the presence of an organic base e.g. triethylamine or an inorganic base, e.g. potassium carbonate, sodium hydroxide, or in pyridine, at room temperature or at the reflux temperature of the reaction mixture.

A preferred method is when the acid of general formula (XVI) is reacted with the amine of general formula (V) in the presence of an activating agent. Activation of the carboxylic acid can be achieved by the preparation of mixed anhydride intermediates with using e.g. pivalyl chloride (M. T. Leplawy: Tetrahedron 1960, 11, 39), ethyl chloroformate (T. Wieland: J. Liebigs Ann. Chem. 1951, 572, 190), isobutyl chloroformate (J. R. Vaughan: JACS. 1951, 73, 3547) or dicyclohexyl carbodiimide (DCC) (R. Arshady: J. Chem. Soc. Perkin Trans. 1, 1981, 529 or D. Hudson: J. Org. Chem. 1988, 53, 617), in inert solvents (e.g. dichloromethane, chloroform, tetrahydrofuran, acetonitrile), in the presence of acid binding tertiary amines (triethylamine, N-methylmorpholine), at a temperature between −10° C. and 25° C.

Activation may also be achieved by use of carbonyl diimidazole (H. A. Staab: Lieb. Ann. Chem.: 1957, 609, 75), in inert solvents, preferably dichloromethane, chloroform, tetrahydrofuran, acetonitrile or in the mixture thereof. Activation can also be carried out with benzotriazol-1-yl-oxy-tripyrrolidinophosphonium hexafluorophosphate (PyBOP) in inert solvent (J. Corte: Tetrahedron Lett. 31, 1990, 205).

If the compound of general formula (XVI) is a carboxylic acid ester, where in the formula W stands for —$OR^{11}$-group, the reaction is performed by methods known in the literature, preferably at 100° C.-150° C., without solvent, in melt.

Scheme 3. presents a third possible process (process version c.), for the preparation of the compounds of general formula (I) where in the formula B means —$NR^6$ group.

chiral preparative column chromatography, or by other methods known for the resolution of compounds of basic character.

The alcohols of the general formula (II) where B represents oxygen atom and the meaning of $Ar^2$ is as defined above are in part known in the literature, or they can be prepared by a method known in the literature. The amines of the general formula (II) where B represents —$NR^6$— and the meanings of $Ar^2$ and $R^6$ are as defined above, are in part known in the literature, or they can be prepared by a method known in the literature or they are commercially available.

Scheme 4. shows the preparation of the compounds of general formula (III).

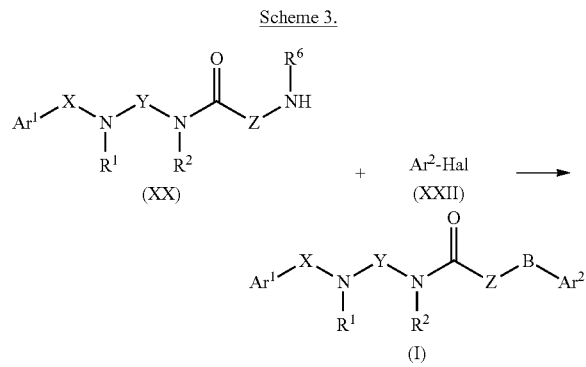

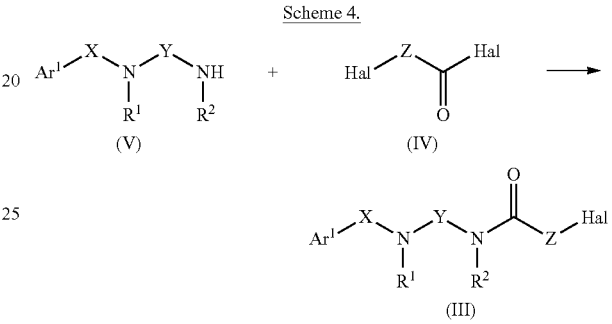

In process version c.) according to the invention for the preparation of compounds of general formula (I) where in the formula B means —$NR^6$— and the meanings of $Ar^1$, X, Y, Z, $R^1$, $R^2$, $R^6$ and $Ar^2$ are as defined above, a compound of general formula (XX),

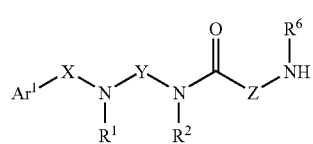

where the meanings of $Ar^1$, X, Y, Z, $R^1$, $R^2$ and $R^6$ are as defined above, is reacted with a halogen compound of general formula (XXII),

where the meaning of $Ar^2$ is as defined above and Hal represents halogen atom, and if desired the substituents of the compound of general formula (I) thus obtained are transformed into each other by using known methods and/or the resulting compound of general formula (I) is transformed into its salt or solvate, or liberated from its salt or solvate and/or resolved into its optically active isomers, or the optically active isomer is transformed into the racemic compound and if desired the structural isomers are separated from each other.

The reaction is preferably carried out in the presence of a base, e.g. triethylamine, diethyl-i-propylamine, in an inert solvent, e.g. dichloromethane, chloroform, tetrahydrofuran, acetonitrile or in the mixture thereof.

If the compound of general formula (I) is a racemic compound, separation of the enantiomers can be carried out by The halogen compounds of general formula (III)—where in the formula the meanings of $Ar^1$, X, $R^1$, Y, $R^2$ and Z are as defined above and Hal stands for halogen atom, preferably chloro or bromo atom—are not described in the literature, but they can be prepared by known methods (e.g. Chem. Pharm. Bull. 2003, 51, 6, 697-701; J. Chem. Soc. Perkin Transl. 1993, 2, 613; JACS. 1947, 69, 515; J. Med. Chem. 1998, 41, 11, 1943) from the diamines of general formula (V)—where in the formula the meanings of $Ar^1$, X, $R^1$, Y, and $R^2$ are as defined above—with the acyl bromides or acyl chlorides of general formula (IV)—where in the formula the meaning of Z is as defined above—by methods known in the literature, in inert solvents, for example in dichloromethane, tetrahydrofuran or acetonitrile or in the mixture thereof, preferably in dichloromethane at room temperature or at lower temperatures. The acyl bromides and acyl chlorides of general formula (IV) are commercially available. The diamines of general formula (V) can be prepared by different methods depending on the nature of the substituents $R^1$, $R^2$, X and Y.

The diamines of the general formula (V), where in the formula $R^2$ stands for hydrogen atom, Y for 1,3-propylene, 1-methyl-1,3-propylene, 2-methyl-1,3-propylene or 1,4-butylene group, ($R^8$ and $R^7$ independently represent hydrogen atom or methyl group, p is 0 or 1) and the meanings of $Ar^1$ and X are as defined above, can be prepared as shown in Scheme 5.

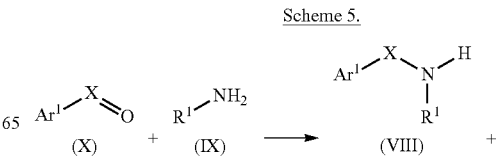

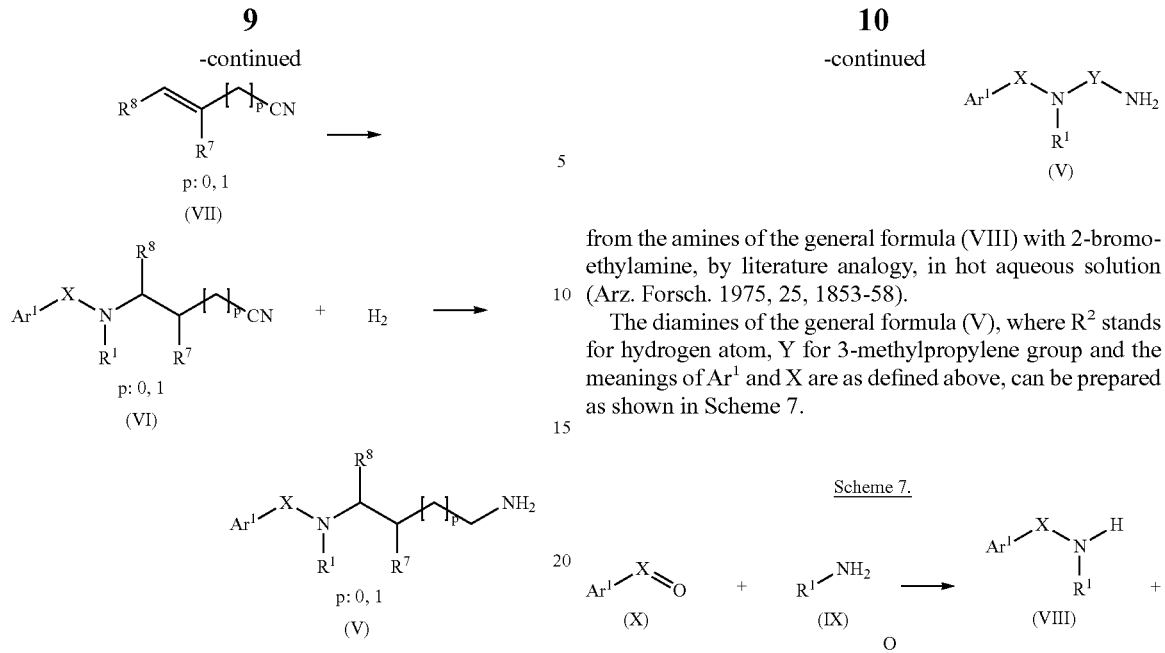

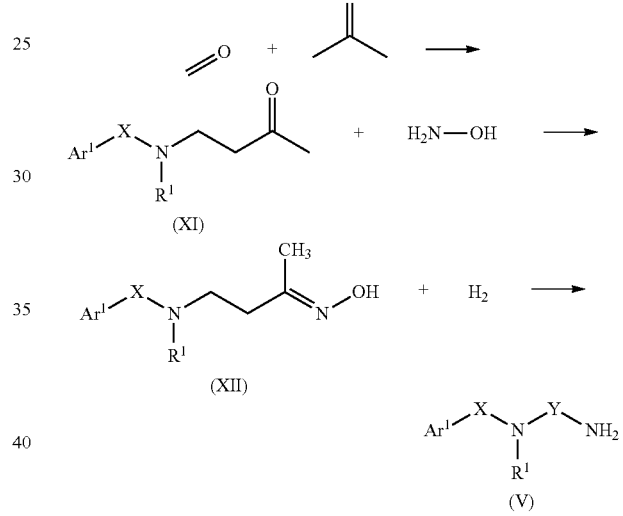

The compounds of the general formula (VIII) can be prepared by methods known in the literature starting from the oxo compounds (aldehydes or ketones) of the general formula (X) by reductive amination with the amines of general formula (IX) in methanol, in the presence of sodium cyanoborohydride (Holzgrabe U.: Arch. Pharm. 1987, 320, 7, 647-654), or by catalytic hydrogenation (Elslager E. F.: J. Med. Chem. 1981, 24, 2, 140-145), or with sodium borohydride in aqueous alcohol medium (Simig Gy.: J. Chem. Soc Perkin Trans. 1. 1992, 13, 1613-16). The compounds of the general formula (IX) are commercially available. The aldehydes of general formula (X) are commercially available or can be prepared by methods known in the literature. The compounds of general formula (VI) can be prepared from the compounds of general formula (VIII) with the alkene-cyanides of the general formula (VII) by literature analogies (King M. et al: JACS. 1946, 68, 1468, or Surrey et al: JACS. 1956, 78, 2573). The cyanides of the general formula (VII) are commercially available. The diamines of the general formula (V) can be obtained by catalytic hydrogenation of the cyanides of general formula (VI) by literature analogies, in alcohol or hexane solution, in the presence of ammonia and Raney nickel or rhodium catalyst, in a given case under pressure (Shapiro et al: JACS. 1959, 81, 3083-84, and Roufos I.: J. Med. Chem. 1996, 39, 7, 1514).

The diamines of the general formula (V), where in the formula the meaning of Y is ethylene group, $R^2$ stands for hydrogen atom and the meanings of $Ar^1$ and X are as defined above, can be prepared as shown in Scheme 6.

Scheme 6.

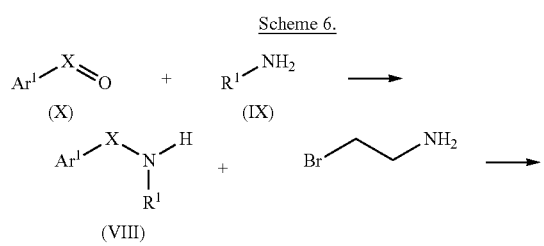

from the amines of the general formula (VIII) with 2-bromo-ethylamine, by literature analogy, in hot aqueous solution (Arz. Forsch. 1975, 25, 1853-58).

The diamines of the general formula (V), where $R^2$ stands for hydrogen atom, Y for 3-methylpropylene group and the meanings of $Ar^1$ and X are as defined above, can be prepared as shown in Scheme 7.

Scheme 7.

The compounds of general formula (XI) are obtained by Mannich condensation from the amines of general formula (VIII) with paraformaldehyde and acetone. By literature analogy, the reaction can be performed in i-propanol under reflux conditions (JACS. 1959, 81, 2214-18). The oximes of general formula (XII) are prepared from the compounds of general formula (XI) with hydroxylamine, by literature analogies, in aqueous i-propanol solution (JACS. 1959, 81, 2214-18). The amine of general formula (V) is prepared by literature analogy from the oxime of general formula (XII) by catalytic hydrogenation in the presence of Raney-Nickel catalyst, in ethanolic ammonia solution.

Scheme 8. demonstrates the preparation of the compounds of general formula (V) where $R^1$ and $R^2$ represents methyl group and the meanings of $Ar^1$, X and Y are as defined above.

Scheme 8.

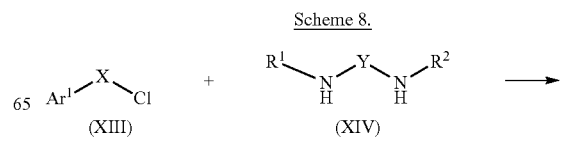

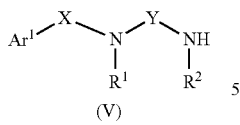

(V)

The compounds of the general formula (V) can be obtained by reacting the commercially available aryl-alkyl halogenides of the general formula (XIII) with the N,N'-dimethylaminoalkyl compounds of general formula (XIV), in inert solvents, preferably in acetonitrile, in the presence of an acid binding organic amine.

The compounds of the general formula (X), where X represents 1,3-propylene group and the meaning of $Ar^1$ is as defined above, can be obtained as presented in Scheme 9., Scheme 9.

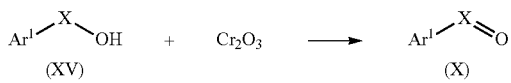

by analogies in the literature (J. Org. Chem. 2002, 67, 25, 8758-8763), from the appropriate alcohols of general formula (XV) by oxidation with pyridinium chlorochromate in inert solvent, preferably in dichloromethane.

The ketones of general formula (X), where X represents 3-methylpropylene group, can be prepared by the method shown in Scheme 10.

Scheme 10.

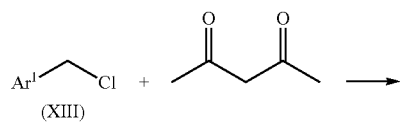

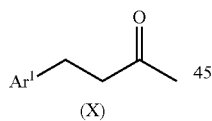

(X)

by analogies in the literature (Powel et al: JACS. 2004, 126, 25, 7788-89), by heating the commercially available benzyl-chlorides of general formula (XIII) with pentane-2,4-dione in alcohol solution under reflux conditions, in the presence of potassium carbonate.

The oxycarboxylic aids of general formula (XVI) are commercially available or can be prepared by the methods known in the literature. Preparation of the (benzoxazol-2-yloxy)acetic acids and their esters is shown in Scheme 11.

Scheme 11.

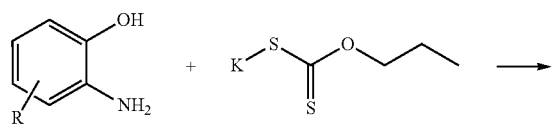

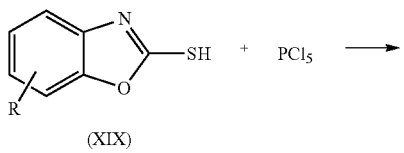

(XIX)

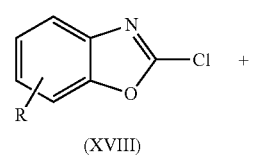

(XVIII)

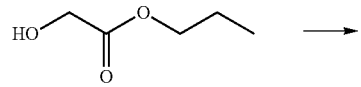

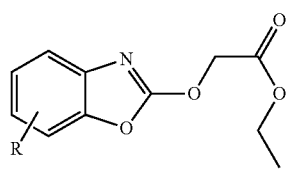

(XVII)

The 2-mercaptobenzoxazole of formula (XIX) can be prepared from the appropriately substituted 2-hydroxyanilines by the methods known in the literature. From that compound with phosphorpentachloride is obtained 2-chlorobenzoxazol of formula (XVIII). (Haviv F. et al.: J. Med. Chem. 31, 9, 1988, 1719; Seidel: J. Prakt. Chem. 2, 1890, 454; Chen et al.: Heteroat. Chem. 12, 3, 2001, 151). The (benzoxazol-2-yloxy) acetic acid esters (XVII) are synthesized from the chloro-compound (XVIII) with glycolic acid ester, (hydroxyacetate) in the presence of sodium hydride at a temperature between 25° C.-50° C. in inert solvent, preferably in tetrahydrofuran.

Preparation of the Compounds of General Formulae (XXI) and (XX) is Demonstrated in Scheme 12.

Scheme 12.

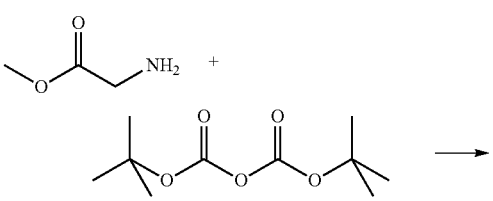

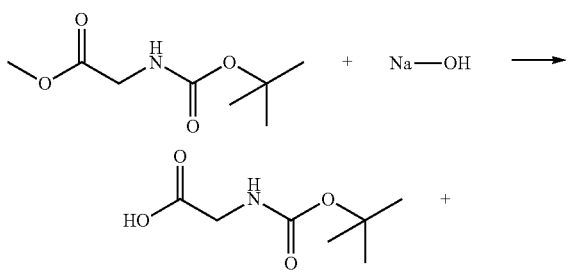

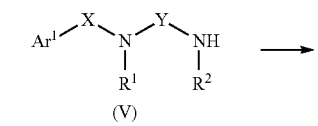

(V)

-continued

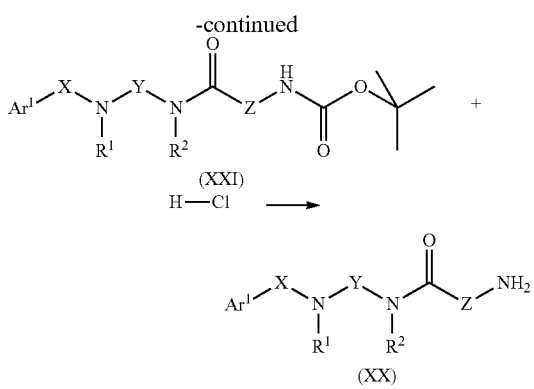

In the first step the glycine methyl ester is protected by a method known in the literature, then the ester function is hydrolyzed. Reaction with the diamine of general formula (V) leads to the novel compound of general formula (XXI), which by acidic hydrolysis results the novel amino derivatives of general formula (XX) where $R^6$ means hydrogen atom, which if desired on alkylation by known methods affords the compounds of general formula (XX) where $R^6$ means $C_{1-4}$ alkyl group.

Further details of the invention are demonstrated by the examples, without limiting the invention to the examples.

EXAMPLES

Example 1

2-(1,3-Benzthiazol-2-yloxy)-N-{3-[(3,4-dichorobenzyl)(methyl)amino]propyl}acetamide In general formula (I) $Ar^1$ stands for 3,4-dichorophenyl group, X and Z for methylene group, $R^1$ for methyl group, Y for 1,3-propylene group, $R^2$ for hydrogen atom, B means oxygen atom, Ar2 represent 1,3-benzothiazol-2-yl group.

a.) 2-Bromo-N-{3-[(3,4-dichlorobenzyl)(methyl)amino]propyl}acetamide a/1.) N-(3,4-Dichlorobenzyl)methylamine hydrogen chloride salt (Simig Gy.: J. Chem. Soc Perkin Trans. 1. 1992, 13, 1613-16) 17.5 g (100 mmol) 3,4-dichlorobenzaldehyde is dissolved in 40 ml methanol and under stirring 15.6 ml 40% aqueous methylamine (200 mmol) in 30 ml methanol is added to it. The reaction mixture is cooled to 0° C. and in small portions 1.9 g (50 mmol) sodium borohydride is added, while keeping the temperature at 0° C. Without cooling-bath the reaction mixture is allowed to reach room temperature and stirring is continued for 28 hours. Methanol is distilled off in vacuum and to the residue 200 ml dichloromethane is added. The mixture is extracted with 3×50 ml water, the organic phase is dried over sodium sulfate and evaporated in vacuum. The crude product is dissolved in 100 ml ethyl acetate and acidified with hydrogen chloride saturated solution in ether (50 ml.) The resulting crystals are filtered off, washed consecutively with ethyl acetate and ether to obtain 20 g of the title compound as white crystals. Mp: 225° C.

a/2.)
3-[(3,4-Dichlorobenzyl)(methyl)amino]propionitrile

From 20 g (88 mmol) N-(3,4-Dichlorobenzyl)methylamine hydrogen chloride salt the base is liberated by the addition of 12.6 ml (90 mmol) triethylamine in 100 ml ethyl acetate solution. The resulting 16.5 g base is dissolved in 170 ml abs. methanol, the solution is cooled to below 0° C. and 5.7 ml (87 mmol) acrylonitrile is added to it. The reaction mixture is stirred at 0° C. for 30 minutes, allowed to reach room temperature, stirred for 30 hours and evaporated to obtain 20 g of the title compound in the form of an oil. LC/MS[MH$^+$]=243 ($C_{11}H_{12}Cl_2N_2$ 243.14).

a/3.) N-(3,4-Dichlorobenzyl)-N-(methyl)propane-1,3-diamine 20 g (82.3 mmol) 3-[(3,4-Dichlorobenzyl)(methyl)amino]propionitrile is hydrogenated at room temperature, in the presence of Raney-Nickel catalyst, in ethanolic ammonia solution in (100 ml). After removal of the solvent 20 g title compound is obtained in the form of an oil. LC/MS[MH$^+$]=247 ($C_{11}H_{16}Cl_2N_2$ 247.17)

a.) 2-Bromo-N-{3-[(3,4-dichlorobenzyl)(methyl)amino]propyl}acetamide hydrogen bromide salt 4.9 g (20 mmol) N-(3,4-Dichlorobenzyl)-N-(methyl)propan-1,3-diamine is dissolved in 50 ml dichloromethane. The solution is cooled to −10° C. and at that temperature 2 ml (23 mmol) bromoacetyl bromide in 12 ml dichloromethane is added to it dropwise. The reaction mixture is stirred at −10° C. for 10 minutes and at room temperature for 3 hours. Dichloromethane is poured off, the residue is stirred with 15 ml abs. ethanol, the precipitated crystals are filtered off, washed with ethanol and with ether to obtain 7 g title compound in the form of its hydrogen bromide salt. Mp.: 141° C.

b.) 2-(1,3-Benzothiazol-2-yloxy)-N-{3-[(3,4-dichlorobenzyl)(methyl)amino]propyl}-acetamide 0.0756 g (0.5 mmol) 1,3-benzothiazol-2-ol is dissolved in 5 ml dimethylformamide, 0.15 g (1.1 mmol) dry potassium carbonate is added and under stirring at room temperature 0.18 g (0.5 mmol) 2-bromo-N-{3-[(3,4-dichlorobenzyl)(methyl)amino]propyl}acetamide in 2 ml dimethylformamide is added dropwise. Stirring is continued for 24 hours. The reaction mixture is poured onto ice-water mixture, the precipitated crystals are filtered off, washed with water to obtain 0.13 g title compound. Mp: 113-115° C.

Example 2

N-{3-[(3,4-Dichlorobenzyl)(methyl)amino]propyl}2-(2,4-dichlorophenoxy)acetamide

In general formula (I) $Ar^1$ stands for 3,4-dichorophenyl group, X and Z for methylene group, $R^1$ for methyl group, Y for 1,3-propylene group, $R^2$ for hydrogen atom, B means oxygen atom, Ar2 represent 2,4-dichlorophenyl group.

To the solution of 0.247 g (1 mmol) N-(3,4-dichlorobenzyl)]-N-(methyl)propane-1,3-diamine in 2 ml chloroform, under stirring and ice-water cooling 0.06 g (1.5 mmol) sodium hydroxide in 1 ml water is added, then the solution of 0.26 g (1.1 mmol) (2,4-dichlorophenoxy)acetyl chloride in 1 ml chloroform is added dropwise. Without cooling stirring is continued for 36 hours. Chloroform is removed, 10 ml water is added and the mixture is extracted with 3×20 ml ethyl acetate. The united organic phase is dried over sodium sulfate and evaporated. The crude product is purified by column chromatography using chloroform-methanol 9:1 mixture as eluent. 0.11 g title compound is obtained as oil. LC/MS [MH$^+$]=449 (C$_{19}$H$_{20}$Cl$_4$N$_2$O$_2$ 450.20).

Example 3

N-{3-[(3,4-Dichlorobenzyl)(methyl)amino]propyl}-2-[(6-methyl-1,3-benzoxazol-2-yl)oxy]acetamide In general formula (I) Ar$^1$ stands for 3,4-dichorophenyl group, X and Z for methylene group, R$^1$ for methyl group, Y for 1,3-propylene group, R$^2$ for hydrogen atom, B means oxygen atom, Ar2 represent 6-methyl-1,3-benzoxazol-2-yl group.

a.) 6-Methylbenzoxazole-2-thiol (Haviv F. et al.: J. Med. Chem. 1988, 31, 9, 1719-28)

3.7 g (30 mmol) 2-hydroxy-4-methylaniline is suspended in 50 ml ethanol, 4.8 g (30 mmol) O-ethyl-xanthic acid potassium salt is added to it and the mixture is heated under reflux conditions for 16 hours. The solvent is removed, the residue is dissolved in water, acidified with acetic acid to pH 5, the precipitated crystals are filtered off, washed with water. 4.3 g title compound is obtained. Mp: 209° C.

b.) 2-Chloro-6-methyl-1,3-benzoxazole (Haviv F. et al.: J. Med. Chem. 1988, 31, 9, 1719-28)

4.1 g (25 mmol) 6-methyl-1,3-benzoxazol-2-thiol is suspended in 40 ml toluene, slowly 6.2 g (30 mmol) phosphor pentachloride is added to it and the mixture is heated under reflux conditions for 16 hours. The solvent is removed, to the residue ether is added, the precipitated inorganic salts are filtered off, the ether solution is evaporated. 2.8 g title compound is obtained in the form of an oil. LC/MS[MH$^+$]=168 (C$_8$H$_6$ClNO 167.59).

c.) Ethyl [(6-Methyl-1,3-benzoxazol-2-yl)oxy]acetate 0.73 g (7 mmol) ethyl hydroxyacetate is dissolved in 20 ml tetrahydrofurane and 0.36 g (9 mmol) 60% sodium hydride is added to it. After 20 minute stirring 1.0 g (6 mmol) 2-chloro-6-methyl-1,3-benzoxazole is added and the mixture is heated under reflux for 3 hours. The solvent is removed, the residue is dissolved in 15 ml water, extracted with 3×20 ml ethyl acetate. The united organic phase is dried over sodium sulfate and evaporated to obtain 1.3 g title compound as an oil. LC-MS[MH$^+$]=236 (C$_{12}$H$_{13}$NO$_4$ 235.24)

d.) N-{3-[(3,4-Dichlorobenzyl)(methyl)amino]propyl}-2-[(6-methyl-1,3-benzoxazol-2-yl)oxy]acetamide The mixture of 1 g (4.6 mmol) ethyl [(6-methyl-1,3-benzoxazol-2-yl)oxy]acetate and 1.13 g (4.6 mmol) N-(3,4-dichlorobenzyl)]-N-(methyl)propane-1,3-diamine is heated at 100° C. for 4 hours. The crude melt is purified by column chromatography using ethyl acetate-pyridine-acetic acid-water 960:20:6:11 mixture as eluent. After evaporation of the fractions the residue is crystallized from hexane-petrolether 1:1 mixture. 75 mg title compound is obtained in the form of white crystals. Mp: 62-66° C.

Example 4

2-[(1,3-Benzoxazol-2-yl)oxy]-N-{3-[(3,4-dichlorobenzyl)(methyl)amino]propyl}acetamide In general formula (I) Ar$^1$ stands for 3,4-dichorophenyl group, X and Z for methylene group, R$^1$ for methyl group, Y for 1,3-propylene group, R$^2$ for hydrogen atom, B means oxygen atom, Ar2 represent 1,3-benzoxazol-2-yl group.

a.) Ethyl[(1,3-benzoxazol-2-yl)oxy]acetate 0.14 g (1.3 mmol) ethyl-hydroxyacetate is dissolved in 5 ml tetrahydrofurane and 0.06 g (1.6 mmol) 60% sodium hydride is added to it. After 20 minute stirring 0.16 g (1.1 mmol) 2-chloro-1,3-benzoxazole is added and the mixture is heated under reflux for 3 hours. The solvent is removed, the residue is dissolved in 15 ml water, extracted with 3×20 ml ethyl acetate. The united organic phase is dried over sodium sulfate and evaporated to obtain 0.21 g title compound as an oil. LC-MS[MH$^+$]=222 (C$_{11}$H$_{11}$NO$_4$ 221.21)

b.) (1,3-Benzoxazol-2-yloxy)acetic acid

The solution of 0.2 g (0.9 mmol) ethyl-(1,3-benzoxazol-2-yloxy)acetate and 0.4 g (1 mmol) sodium hydroxide in 1 ml water is stirred for 2 hours at room temperature, then extracted with 3×5 ml chloroform. The united organic phase is dried over sodium sulfate and evaporated in vacuum to obtain 54 mg title compound as an oil. LC-MS[MH$^+$]=194 (C$_9$H$_7$NO$_4$ 193.16)

c.) 2-(1,3-Benzoxazol-2-yloxy)-N-{3-[(3,4-Dichlorobenzyl)(methyl)amino]propyl}acetamide To the solution of 54 mg (0.28 mmol) (1,3-benzoxazol-2-yloxy)acetic acid in 3 ml chloroform 28 mg (0.28 mmol) 4-methylmorpholine is added. The mixture is cooled to −15° C., 30 mg (0.28 mmol) ethyl chloroformate is dropped to it and the mixture is stirred under cooling for 15 minutes. Then the solution of 83 mg (0.34 mmol) N-(3,4-dichlorobenzyl)-N-(methyl)propane-1,3-diamine in 2 ml chloroform is added and the reaction mixture is stirred for 30 min under cooling and 1 hour at room temperature. The chloroform solution is extracted with 2×10 ml water, the organic phase is dried over sodium sulfate and evaporated in vacuum to obtain 50 mg title compound as an oil. LC/MS[MH$^+$]=422 (C$_{20}$H$_{21}$Cl$_2$N$_3$O$_3$ 422.31).

Example 5

N-{3-[(3,4-Dichlorobenzyl)(methyl)amino]propyl}-2-[1-(4-methoxybenzyl)-1H-benzimidazol-2-yloxy]acetamide In general formula (I) Ar$^1$ stands for 3,4-dichorophenyl group, X and Z for methylene group, R$^1$ for methyl group, Y for 1,3-propylene group, R$^2$ for hydrogen atom, B means oxygen atom, Ar2 represent [1-(4-methoxybenzyl)-1H-benzimidazol-2-yl] group.

The title compound is prepared according to the method described in Example 4. c.), starting from 0.15 g (0.48 mmol) {[1-(4-methoxybenzyl)-1H-benzimidazol-2-yl]oxy}acetic acid, 0.13 g (0.52 mmol) N-(3,4-dichlorobenzyl)-N-(methyl)propane-1,3-diamine, 0.048 g (0.48 mmol) 4-methylmorpho-

Example 6

N-{3-[(3,4-Dichlorobenzyl)(methyl)amino]propyl}-3-benzylamino]propionamide

In general formula (I) $Ar^1$ stands for 3,4-dichorophenyl group, X for methylene group, $R^1$ for methyl group, Y for 1,3-propylene group, $R^2$ for hydrogen atom, Z for ethylene group, B means —NH— group, $Ar^2$ represent benzyl group. The mixture of 0.2 g (1 mmol) ethyl (3-benzylamino)propionate and 0.24 g (1 mmol) N-(3,4-dichlorobenzyl)-N-(methyl)propane-1,3-diamine is heated at 100° C. for 6 hours. The crude melt is purified by column chromatography. 60 mg title compound is obtained in the form of oil. LC/MS[MH+]=408 ($C_{21}H_{27}Cl_2 N_3O$ 408.37).

Example 7

$N^2$-1,3-benzothiazol-2-yl-$N^1$-{3-[(3,4-Dichlorobenzyl)(methyl)amino]propyl}glycinamide

In general formula (I) $Ar^1$ stands for 3,4-dichorophenyl group, X and Z for methylene group, $R^1$ for methyl group, Y for 1,3-propylene group, $R^2$ for hydrogen atom, B means —NH— group, $Ar^2$ represent 1,3-benzothiazol-2-yl group.

a.) 1,3-Benzothiazol-2-ylformamide (Huffmann: J. Org. Chem. 1958, 23, 727)
The mixture of acetic anhydride and 98% formic acid is heated at 60° C. for 2 hours. To 4.4 g (50 mmol) of the resulting anhydride 3.75 g (25 mmol) 2-amino-1,3-benzothiazole is added at room temperature during 15 minutes while keeping the temperature below 40° C. Then 12 ml ether is added and the mixture is stirred at room temperature for 12 hours. The precipitated crystals are filtered off and washed with ether to obtain 4 g title compound. LC/MS[MH+]=179 ($C_8H_6N_2OS$ 178.214).

b.) Ethyl N-1,3-benzothiazol-2-ylglycinate

To the suspension of 0.2 g (5 mmol) 60% sodium hydride in 5 ml dimethylformamide in small portions 0.89 g (5 mmol) 1,3-benzothiazol-2-ylformamide, then after 30 minutes of stirring, dropwise the solution of 0.92 g (5.5 mmol) ethyl bromoacetate in 2 ml dimethylformamide are added and the mixture is stirred at room temperature for 4 hours. The reaction mixture is poured onto ice-water mixture, the precipitated crystals are filtered off. 0.85 g title compound is obtained. LC/MS[MH+]=237 ($C_{11}H_{12}N_2O_2S$ 236.294).
The mixture of $N^2$-1,3-benzothiazol-2-yl-$N^1$-{3-[(3,4-dichlorobenzyl)(methyl)amino]propyl}glicinamide 0.68 g (2.88 mmol) ethyl N-1,3-benzothiazol-2-ylglicinate and 0.81 g (2.88 mmol) N-(3,4-dichlorobenzyl)-N-(methyl)propane-1,3-diamine is heated at 100° C. for 2 hours. The crude melt is purified by column chromatography using chloroform-methanol 19:1 mixture as eluent. 500 mg title compound is obtained as crystals.
Mp: 91-97° C.

Example 8

$N^2$-1,3-benzoxazol-2-yl-$N^1$-{3-[(dichlorobenzyl)(methyl)amino]propyl}glycinamide

In general formula (I) $Ar^1$ stands for 3,4-dichorophenyl group, X and Z for methylene group, $R^1$ for methyl group, Y for 1,3-propylene group, $R^2$ for hydrogen atom, B means —NH— group, Ar2 represent 1,3-benzoxazol-2-yl group.

a.) Methyl N-1,3-benzoxazol-2-ylglycinate (for the ethyl ester see: Advani S. P. et al.: J. Pharm. Sci. 1968, 57, 1693-96)
To the solution of 1.26 g (10 mmol) methyl glycinate in 10 ml chloroform 1.31 g (13 mmol) triethylamine, then 0.76 g (5 mmol) 2-chloro-1,3-benzoxazole are added and the mixture is stirred at 40° C. for 4 hours and at room temperature for 12 hours. The chloroform solution is washed with water, citric acid solution and water, dried over sodium sulfate and evaporated in vacuum. The residue is treated with hexane, the crystals are filtered off and washed. 0.55 g title compound is obtained as white crystals. Mp: 103-106° C.
$N^2$-1,3-benzoxazol-2-yl-$N^1$-{3-[(3,4-dichlorobenzyl)(methyl)amino]propyl}glycinamide 0.24 g (1 mmol) methyl N-1,3-benzoxazol-2-ylglicinate and 0.2 g (1 mmol) N-(3,4-dichlorobenzyl)-N-(methyl)propane-1,3-diamine is heated at 100° C. for 12 hours. The crude melt is purified by column chromatography using chloroform-methanol 9:1 mixture as eluent. 130 mg title compound is obtained as crystals. Mp: 97-98° C.

Example 9

$N^2$-1,3-benzoxazol-2-yl-$N^1$-{3-[(3,4-dichlorobenzyl)(methyl)amino]propyl}alaninamide

In general formula (I) $Ar^1$ stands for 3,4-dichorophenyl group, X for methylene group, $R^1$ for methyl group, Y for 1,3-propylene group, $R^2$ for hydrogen atom, Z for —CH($CH_3$)-group, B means —NH— group, $Ar^2$ represent 1,3-benzoxazol-2-yl group.

a.) Methyl-N-1,3-benzoxazol-2-ylalaninate

To the suspension of 0.62 g (6 mmol) methyl alaninate hydrogen chloride salt and 4 ml chloroform 0.79 g (7.8 mmol) triethylamine and 0.46 g (3 mmol) 2-chloro-1,3-benzoxazole are added and the mixture is stirred at 40° C. for 4 hours and at room temperature for 12 hours. The chloroform solution is washed with water, citric acid solution and water, dried over sodium sulfate and evaporated in vacuum. The residue is treated with hexane, the crystals are filtered off and washed. 0.11 g title compound is obtained as white crystals. Mp: 112-113° C.

b.) $N^2$-1,3-benzoxazol-2-yl-$N^1$-{3-[(dichlorobenzyl)(methyl)amino]propyl}-alaninamide The mixture of 0.11 g (0.5 mmol) methyl-N-1,3-benzoxazol-2-ylalaninate and 0.12 g (0.5 mmol) N-(3,4-dichlorobenzyl)-N-(methyl)propane-1,3-diamine is heated at 100° C. for 12 hours. The crude melt is purified by column chromatography

--- line and 0.052 g (0.48 mmol) ethyl chloroformate. 17 mg product is obtained as oil. LC/MS[MH+]=541 ($C_{28}H_{30}Cl_2 N_4O_3$ 541.476).

using chloroform-methanol 98:2 mixture as eluent. 90 mg title compound is obtained as crystals. Mp: 117-118° C.

Example 10

N³-1,3-benzoxazol-2-yl-N¹-{3-[(3,4-dichorobenzyl)(methyl)amino]propyl}-β-alaninamide In general formula (I) Ar¹ stands for 3,4-dichorophenyl group, X for methylene group, R¹ for methyl group, Y for 1,3-propylene group, R² for hydrogen atom, Z for ethylene group, B means —NH group, Ar² represent 1,3-benzoxazol-2-yl group.

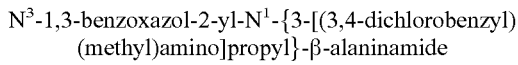

a.) Methyl-N-1,3-benzoxazol-2-yl-β-alaninate

To the suspension of 0.55 g (4 mmol) methyl □-alaninate hydrogen chloride salt and 4 ml chloroform 0.52 g (5.2 mmol) triethylamine and 0.3 g (2 mmol) 2-chloro-1,3-benzoxazole are added and the mixture is stirred at 40° C. for 4 hours and at room temperature for 12 hours. The chloroform solution is washed with water, citric acid solution and water, dried over sodium sulfate and evaporated in vacuum. The residue is treated with hexane, the crystals are filtered off and washed. 0.11 g title compound is obtained as white crystals. Mp: 110-112° C.

b.) N³-1,3-benzoxazol-2-yl-N-{3-[(dichlorobenzyl)(methyl)amino]propyl}-3-alaninamide The mixture of 0.11 g (0.5 mmol) methyl-N-1,3-benzoxazol-2-yl-β-alaninate and 0.12 g (0.6 mmol) N-(3,4-dichlorobenzyl)-N-(methyl)propane-1,3-diamine is heated at 100° C. for 12 hours. The crude melt is purified by column chromatography using chloroform-methanol 100:1 mixture as eluent. 103 mg title compound is obtained in the form of crystals. Mp: 76.5-79.5° C.

Example 11

N-{3-[(3,4-Dichlorobenzyl)(methyl)amino]propyl}-3-[(1,3-benzoxazol-2-il)amino]-2-methylpropionamide In general formula (I) Ar¹ stands for 3,4-dichlorophenyl group, X for methylene group, R¹ for methyl group, Y for 1,3-propylene group, R² for hydrogen atom, Z for —CH(CH₃)—CH₂-group, B means —NH— group, Ar² represent 1,3-benzoxazol-2-yl group.

a.) Methyl-3-amino-2-methylpropionate hydrogen chloride salt (Sim M. M. et al.: J. Org. Chem. 1997, 62, 26, 9358)
The solution of 1 g (10 mmol) 3-amino-2-methylpropionic acid in 15 ml methanol is cooled to −10° C., 1 ml (13.7 mmol) thionyl chloride is added to it dropwise and the mixture is heated under reflux for 1 hour. The solvent is removed in vacuum, the residue is crystallized with ether, the crystals are filtered off. 1.23 g title compound is obtained as white crystals. Mp: 107-110° C.

b.) Methyl-3-[(1,3-benzoxazol-2-yl)amino]-2-methylpropionate

To the suspension of 0.55 g (4 mmol) methy 3-amino-2-methylpropionate hydrogen chloride salt and 4 ml chloroform 0.52 g (5.2 mmol) triethylamine and 0.3 g (2 mmol) 2-chloro-1,3-benzoxazole are added and the mixture is stirred at 40° C. for 4 hours and at room temperature for 12 hours. The chloroform solution is washed with water, citric acid solution and water, dried over sodium sulfate and evaporated in vacuum. The residue is treated with hexane, the crystals are filtered off and washed. 0.33 g title compound is obtained as white crystals. Mp: 89-90° C.

c.) N-{3-[(3,4-Dichlorobenzyl)(methyl)amino]propyl}-3-[(1,3-benzoxazol-2-yl)amino]-2-methylpropionamide The mixture of 0.11 g (0.5 mmol) methyl 3-[(1,3-benzoxazol-2-yl)amino]propionate and 0.14 g (0.6 mmol) N-(3,4-dichlorobenzyl)-N-(methyl)propane-1,3-diamine is heated at 100° C. for 2 hours. The crude melt is purified by column chromatography using chloroform-methanol 100:1 mixture as eluent. 50 mg title compound is obtained in the form of crystals. Mp: 134-135° C.

Example 12

N¹-{3-[(3,4-Dichlorobenzyl)(methyl)amino]propyl-N²-(6-methyl-1,3-benzothiazol-2-yl)glycinamide In general formula (I) Ar¹ stands for 3,4-dichlorophenyl group, X and Z for methylene group, R¹ for methyl group, Y for 1,3-propylene group, R² for hydrogen atom, B means —NH— group, Ar2 represent 6-methyl-1,3-benzthiazol-2-yl group.

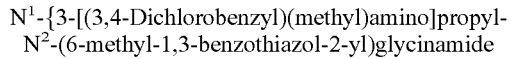

The solution of 0.48 g (1 mmol) 2-bromo-N-{3-[(3,4-dichlorobenzyl)(methyl)amino]propyl}acetamide, 10 ml toluene, 5 ml dimethylformamide and 0.16 g (1 mmol) 2-amino-6-methyl-1,3-benzothiazol is stirred at 90° C. for 5 hours. The solvent is removed in vacuum, the residue is treated with ethyl acetate, the solid material is filtered off, purified by column chromatography using chloroform-methanol 19:1 mixture as eluent. 91 mg title compound is obtained in the form of oil.
LC/MS[MH⁺]=451 (C₂₁H₂₄Cl₂N₄OS 451.42).

Example 13

N¹-{3-[(3,4-Dichlorobenzyl)(methyl)amino]propyl—N²-(6-methyl-1,3-benzoxazol-2-yl)-glycinamide In general formula (I) Ar¹ stands for 3,4-dichlorophenyl group, X and Z for methylene group, R¹ for methyl group, Y for 1,3-propylene group, R² for hydrogen atom, B means —NH— group, Ar2 represent 6-methyl-1,3-benzoxazol-2-yl group.

a.) N¹-{3-[(3,4-Dichlorobenzyl)(methyl)amino]propyl}glycinamide a/1.) Methyl N-(tert-butoxycarbonyl)glycinate (See also: Wiles C. et al.: Tetrahedron, 2003, 59, 51, 10173-180 and McNulty et al.: Synth. Comm., 1992, 22, 7, 975-985)

To the suspension of 2.26 g (18 mmol) glycine methyl ester hydrogen chloride salt in 40 ml tetrahydrofuran 3.8 g (37.4 mmol) 4-methylmorpholine, then in small portions 4.3 g (20 mmol) di-tert-butylcarbonate are added and the mixture is stirred at room temperature for 12 hours. The precipitated morpholine salts are filtered off, the mother liquor is evaporated in vacuum. The residue is dissolved in 50 ml ethyl

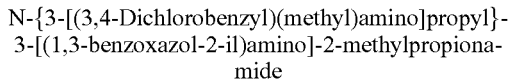

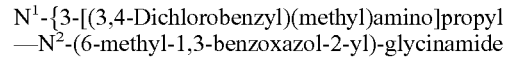

acetate, washed with water and citric acid solution, dried over sodium sulfate and evaporated.

3.7 g title compound is obtained as oil. LC/MS[MH$^+$]=190 ($C_8H_{15}NO_4$ 189.21)

a/2.) N-(tert-butoxycarbonyl)glycine (See also: Klengel H. Et al.: Z. Chem. 1973, 13, 221-22)

3.4 g (18 mmol) methyl N-(tert-butoxycarbonyl)glycinate is dissolved in 30 ml methanol, 20 ml 1N sodium hydroxide solution is added to it, and the mixture is stirred at room temperature for 1 hour. Methanol is distilled off in vacuum and to remove the impurities, the aqueous solution is extracted with ethyl acetate. The aqueous phase is then acidified with solid potassium hydrogensulfate and extracted with ethyl acetate. The organic phase is washed with water, dried over sodium sulfate and evaporated. The residue is crystallized in ether, the crystals are filtered off. 2.3 g title compound is obtained as white crystals. Mp: 89-91° C.

a/3.) tert-Butyl-[2-({3-[(Dichlorobenzyl)(methyl) amino]propyl}amino)-2-oxoethyl]-carbamate To the solution of 1.75 g (10 mm61) N-(tert-butoxycarbonyl) glycine in 15 ml chloroform 1 g (10 mmol) 4-methylmorpholine is added and the mixture is cooled to –15° C. 1 g (10 mmol) ethyl chloformate is added dropwise, then after 15 minutes of cooling and stirring at that temperature 2.6 g (10.5 mmol) N-(3,4-dichlorobenzyl)-N-(methyl)propane-1,3-diamine dissolved in 2 ml chloroform are added. Stirring is continued for 15 minutes under cooling and 1 hour at room temperature. The organic phase is washed with water, citric acid solution, and water, dried over sodium sulfate and evaporated in vacuum. The crude product is purified by column chromatography using chloroform-methanol 98:2 mixture as eluent. 1.3 g title compound is obtained as oil. LC/MS [MH$^+$]=404 ($Cl_8H_{27}N_3O_3$ 404.335).

a.) $N^1$-{3-[(3,4-Dichlorobenzyl)(methyl)amino] propyl}glycinamide hydrogen chloride salt 1.3 g (3.22 mmol) tert-Butyl-[2-({3-[(dichlorobenzyl)(methyl)amino]propyl}amino)-2-oxoethyl]carbamate is dissolved in 5 ml ethanol and saturated hydrogen chloride in ether solution is added to it. The mixture is stirred at room temperature for 1 hour, then the ether phase is several times decanted. 0.6 g title compound is obtained as oil. LC/MS [MH$^+$]=304 ($Cl_{13}H_{20}Cl_3N_3O$ 340.68).

b.) $N^1$-{3-[(3,4-Dichlorobenzyl)(methyl)amino]propyl —$N^2$-(6-methyl-1,3-benzoxazol-2-yl)glycinamide To the solution of 0.22 g (0.67 mmol) $N^1$-{3-[(3,4-dichlorobenzyl)(methyl)amino]propyl}glycinamide hydrogen chloride salt in 5 ml chloroform 0.88 g (0.87 mmol) triethylamine and 0.1 g (0.6 mmol) 2-chloro-6-methyl-1,3-benzoxazole (may be prepared according to Example 3.b.) are added and the mixture is stirred at 50° C. for 12 hours. The solution is washed with water, dried over sodium sulfate and evaporated in vacuum. The residue is crystallized from hexane. 17 mg title compound is obtained. Mp: 126-127° C.

Example 14

In known methods the tablet of the following composition is prepared:

| | |
|---|---|
| Active component: | 40 mg |
| Lactose: | 35 mg |
| Avicel: | 21 mg |
| Crospovidone: | 3 mg |
| Magnesium stearate: | 1 mg |

Example 15

A.) Human recombinant CCR3 receptor (hr-CCR3) binding assay

The CCR3 receptor antagonist effect of the compounds of general formula (I) was examined on eotaxin binding test on hCCR3 receptor expressing recombinant K562 and RBL2H3 cells. To the tests Eotaxin labelled with radioactive iodine $^{125}$I-(2200 Ci/mmol) was used.

In the assay 200000 cells are incubated in the presence of 0.11 nM $^{125}$I-Eotaxin, incubation: 60 minutes at 37° C. Composition of the assay buffer: RPMI-1640 medium, pH=7.6 (GIBCO), [containing 80 mg CHAPS, 500 BSA (protease free), 100 mg Gelatine, 3 ml 25 mM HEPES in 100 ml RPMI]. The test compounds are dissolved in DMSO, the stock solution is diluted with the assay buffer. The final DMSO concentration is not more than 1%. The assays are performed in deep-well plates. The cells are incubated with the test compounds for 15 minutes, then the labelled eotaxin is added. The non-specific binding is determined in the presence of 200 nM non-labelled eotaxin. After 1 hour of incubation, 500 µl ice-cold assay buffer containing 0.5 M NaCl solution is added. The reaction is terminated by centrifugation in plate centrifuge (JUAN) at 3600 g for 6 minutes. The supernatants are poured off by turning the plates in upside-down position. The remaining droplets were blotted with tissue paper. For solubilization 200 µl 0.5 M NaOH solution is added to the pellets. After 1 hour of solubilization at room temperature the radioactivity of 150 µl solubilized solution is counted in gamma counter (1470 Wizard, Wallac).

The radioactivity of the solution is in direct ratio with the number of the receptors of the cells, with the amount of the bound $^{125}$I-Eotaxin and with the activity of the tested antagonist.

The specific binding is calculated as the difference between the total and the non-specific bindings. The activity of the compounds is calculated from the specific binding and from the binding measured in the presence of the antagonist molecule.

The activity of the compounds is characterized with the $IC_{50}$ value.

B.) Investiation of $Ca^{2+}$ Mobilization in hCCR3-RBL and hCCR3K562 Cells HCCR3-K562 and hCCE3-RBL2H3 cells in 40000 cells/well density (number of cells in one well of the microplate) are cultured for 24 hours. The cells are washed and loaded with calcium indicator dye (Calcium Plus assay Kit, Molecular Devices). The cells are incubated in the presence of the dye for 60 minutes while loading takes place. The dye is a fluorescent calcium indicator, which sensitively indicates the intracellular calcium concentration. The intracellular calcium concentration is in direct ratio with the fluorescent signal of the sample. The experiments are performed in a BMG NOVOSTAR apparatus, at excitation and emission wavelengths.

The selective agonists used in the experiments are:
Eotaxin
Eotaxin-2
Eotaxin-3
RANTES Following the addition of the selective agonist, the intracellular calcium concentration in the cells significantly increases which can be monitored with the help of the fluorescent signal. In the experiments an agonist concentration is used which causes a 75% calcium signal compared to the maximum attainable signal.

Antagonists are added 15 minutes before the agonist treatment.

The change of the fluorescent signal is monitored for 30 seconds, during that period the process takes place.

The intensity of the maximum signal following the addition of the agonist is compared with the calcium signal obtained after the addition of the same agonist, but in the presence of the inhibitor.

The activity of the compounds is characterized with the $IC_{50}$ values.

On the basis of tests A and B the compounds of general formula (I) were found biologically active. $IC_{50}$ values of the most potent compounds are in the range of 15 nM to 500 nM.

The invention claimed is:

1. A compound of the general formula (I),

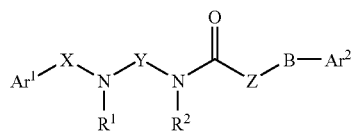

(I)

wherein
B stands for oxygen atom or —$NR^6$ group, wherein $R^6$ means hydrogen atom or straight or branched $C_{1-4}$ alkyl group;
$Ar^1$ stands for phenyl group optionally substituted with one or more halogen atom;
X and Y independently mean straight $C_{1-4}$ alkylene group optionally substituted with one or more identical or non-identical straight or branched $C_{1-4}$ alkyl group;
Z stands for a straight $C_{1-4}$ alkylene group optionally substituted with one or more identical or non-identical straight or branched $C_{1-4}$ alkyl group;
$R^1$ and $R^2$ independently mean hydrogen atom or straight or branched $C_{1-4}$ alkyl group;
$Ar^2$ stands for phenyl group or benzyl group, optionally substituted with halogen atom; or
benzene-fused to 5-membered heterocyclic ring;
wherein the benzene ring group may optionally be further substituted with one or more identical or non-identical substituents selected from the group consisting of straight or branched $C_{1-4}$ alkyl group, straight or branched $C_{1-4}$ alkoxy group, hydroxyl group, amino group, amino group-substituted with one or two identical or non-identical straight or branched $C_{1-4}$ alkyl group-, and halogen atom;
or
a salt or isomer thereof, salt of the isomer thereof.

2. The compound of the general formula (I) according to claim 1 selected from
N-{3-[(3,4-Dichlorobenzyl)(methyl)amino]propyl}-2-(1,3-benzoxazol-2-yl)-amino]acetamide;
$N^1$-{3-[(3,4-Dichlorobenzyl)(methyl)amino]propyl-$N^2$-(6-methyl-1,3-benzothiazol-2-yl)-glycinamide;
2-[(1,3-Benzoxazol-2-yl)oxy]-N-{(3,4-dichlorobenzyl)(methyl)amino]propyl}-acetamide; and
2-(1,3-Benzthiazol-2-yloxy)-N-{3-[(3,4-dichlorobenzyl)(methyl)amino]propyl}acetamide; or a salt or isomer thereof or salt of the isomer thereof.

3. A pharmaceutical composition comprising one or more of the compounds of the general formula (I), according to claim 1, or a salt or isomer thereof or salt of the solvate or isomer thereof, and one or more excipients used in the pharmaceutical industry.

4. The pharmaceutical composition according to claim 3, wherein the one or more compounds of the general formula (I) is/are selected from
N-{3-[(3,4-Dichlorobenzyl)(methyl)amino]propyl}-2-(1,3-benzoxazol-2-yl)-amino]acetamide;
$N^1$-{3-[(3,4-Dichlorobenzyl)(methyl)amino]propyl-$N^2$-(6-methyl-1,3-benzothiazol-2-yl)-glycinamide;
2-[(1,3-Benzoxazol-2-yl)oxy]-N-{(3,4-dichlorobenzyl)(methyl)amino]propyl}-acetamide; and
2-(1,3-Benzthiazol-2-yloxy)-N-{3-[(3,4-dichlorobenzyl)(methyl)amino]propyl}acetamide; or a salt-or isomer thereof, salt of the isomer thereof.

* * * * *